(12) United States Patent
Williams et al.

(10) Patent No.: US 7,147,653 B2
(45) Date of Patent: Dec. 12, 2006

(54) PAD LIKE DEVICE FOR USE DURING PHOTOTHERAPY TREATMENT

(75) Inventors: Jeffrey B. Williams, Ravenna, OH (US); James T. Burke, Brooklyn, OH (US)

(73) Assignee: Lumitex, Inc., Strongsville, OH (US)

( * ) Notice: Subject to any disclaimer, the term of this patent is extended or adjusted under 35 U.S.C. 154(b) by 476 days.

(21) Appl. No.: 10/226,424

(22) Filed: Aug. 23, 2002

(65) Prior Publication Data

US 2004/0039428 A1 Feb. 26, 2004

(51) Int. Cl.
*A61N 5/06* (2006.01)

(52) U.S. Cl. .......................................... 607/88; 607/91

(58) Field of Classification Search ............ 607/88–91, 607/94, 96; 606/9; 219/528, 539; 5/705, 5/706, 4
See application file for complete search history.

(56) References Cited

U.S. PATENT DOCUMENTS

| | | | | | |
|---|---|---|---|---|---|
| 3,877,437 | A | * | 4/1975 | Maitan et al. | 607/91 |
| 4,234,907 | A | * | 11/1980 | Daniel | 362/556 |
| 4,907,132 | A | * | 3/1990 | Parker | 362/556 |
| 5,005,108 | A | * | 4/1991 | Pristash et al. | 362/31 |
| 5,138,138 | A | * | 8/1992 | Theilacker et al. | 219/528 |
| 5,339,223 | A | * | 8/1994 | Kremenchugsky et al. | 362/572 |
| 5,901,391 | A | * | 5/1999 | Kato | 5/666 |
| 6,030,089 | A | | 2/2000 | Parker et al. | |
| 6,045,575 | A | * | 4/2000 | Rosen et al. | 607/88 |
| 6,290,713 | B1 | * | 9/2001 | Russell | 607/88 |
| 6,596,016 | B1 | * | 7/2003 | Vreman et al. | 607/88 |
| 6,641,601 | B1 | * | 11/2003 | Augustine et al. | 607/96 |
| 6,811,563 | B1 | * | 11/2004 | Savage, Jr. et al. | 607/88 |
| 6,916,676 | B1 | * | 7/2005 | Sano et al. | 438/46 |
| 6,939,502 | B1 | * | 9/2005 | Lyden | 264/496 |
| 6,958,494 | B1 | * | 10/2005 | Lin et al. | 257/86 |

* cited by examiner

*Primary Examiner*—A. Farah
(74) *Attorney, Agent, or Firm*—Renner, Otto, Boisselle & Sklar, LLP

(57) ABSTRACT

A pad like device adapted to be placed over a phototherapy light source contains a medium that provides a comfortable support for a patient during phototherapy treatment and allows a portion of the light emitted by the light source to pass through the pad for phototherapy treatment.

29 Claims, 4 Drawing Sheets

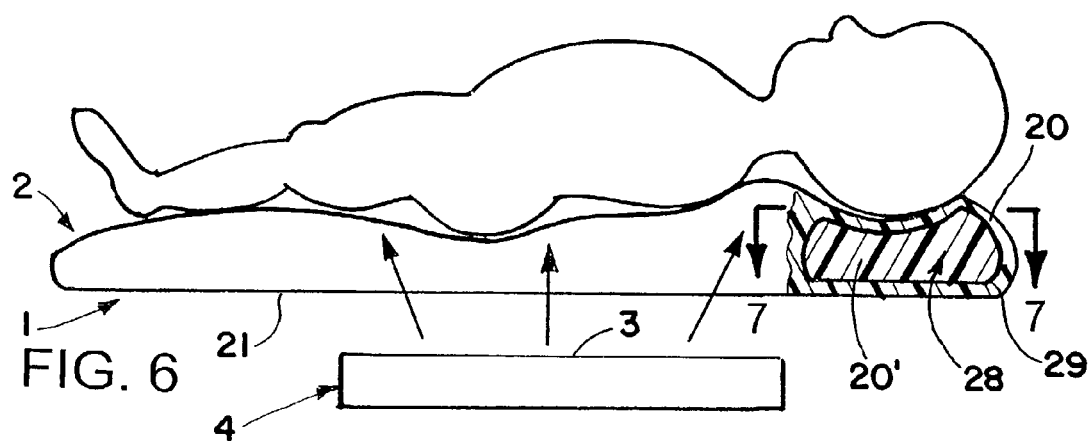
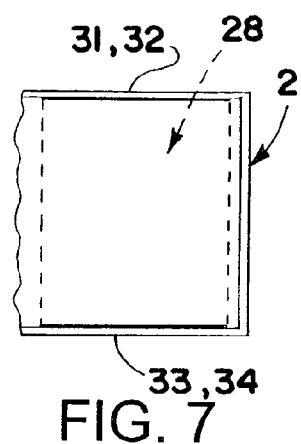
FIG. 6
FIG. 7
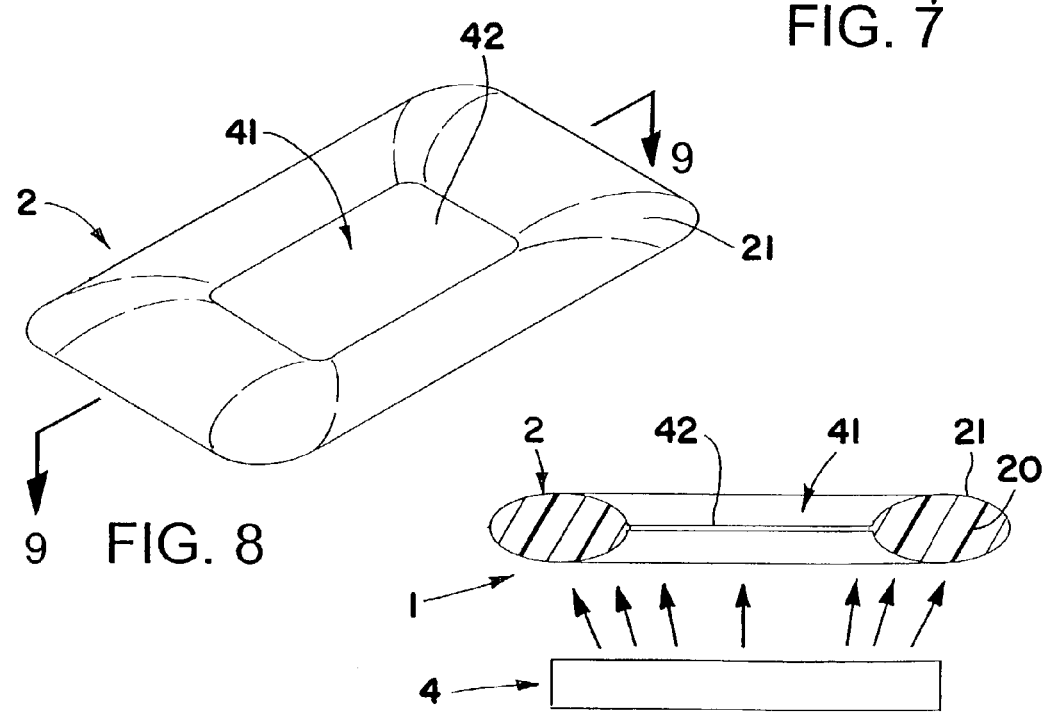
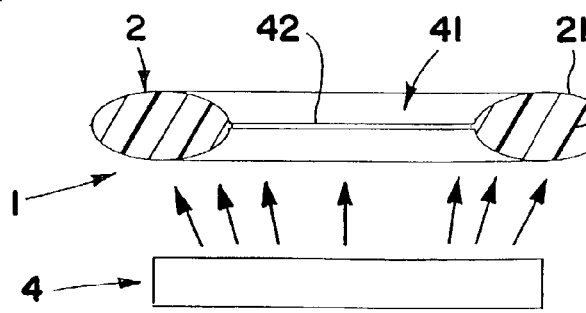
FIG. 8
FIG. 9

PAD LIKE DEVICE FOR USE DURING PHOTOTHERAPY TREATMENT

FIELD OF THE INVENTION

This invention relates to a pad like device that may be placed over a phototherapy light emitter to provide a comfortable support for a human patient during phototherapy treatment.

BACKGROUND OF THE INVENTION

Phototherapy has long been used to treat various human conditions, including for example jaundice in newborn infants. Jaundice is caused by a build up of bilirubin in the blood of infants. Exposing the infant's skin to certain types of light will quickly reduce the bilirubin to a safe level. Such treatment is generally only needed for a few days, until the infant's liver is mature enough to process the bilirubin.

One type of phototherapy light emitter that is commonly used in phototherapy treatment of jaundice in newborn infants comprises a small flexible fiber optic light pad that has a disposable cover to provide a clean surface against the infant's skin. Also, it is known to use a wrap-around vest to securely hold the fiber optic light pad in place against the infant's skin. However, there is a need for a pad like device that can be used with different types of light emitters for phototherapy treatment including both flexible and rigid light emitters that provides a more comfortable support for the patient during phototherapy treatment.

SUMMARY OF THE INVENTION

The device of the present invention comprises a pad like device that is adapted to be placed over a phototherapy light emitter to provide a more comfortable support for a patient during phototherapy treatment.

In accordance with one aspect of the invention, the support pad contains one or more mediums that provide comfort and proper support for the patient during phototherapy treatment.

In accordance with another aspect of the invention, the support pad has one or more transparent or translucent areas that allow light from the phototherapy light emitter to pass through the support pad during phototherapy treatment.

In accordance with another aspect of the invention, the support pad may have areas of different thickness and/or firmness for proper patient support.

In accordance with another aspect of the invention, different areas within the support pad may contain mediums of different firmness or densities for proper patient support.

In accordance with another aspect of the invention, the support pad may have a pocket on one side for receipt of the phototherapy light emitter.

In accordance with another aspect of the invention, the support pad may contain one or more holes or transparent or translucent windows to allow a greater portion of the light from the phototherapy light emitter to pass through these areas of the support pad during phototherapy treatment.

In accordance with another aspect of the invention, the support pad may have one or more opaque or reflective areas for blocking the passage of light from the phototherapy light emitter through the pad in these areas during phototherapy treatment.

In accordance with another aspect of the invention, various attachment devices may be used to attach the phototherapy light emitter to the support pad and to attach the support pad to a patient.

In accordance with another aspect of the invention, the support pad may be internally heated or cooled as needed for patient comfort.

These and other objects, advantages, features and aspects of the invention will become apparent as the following description proceeds.

To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 2 is a schematic perspective view showing the pad like device placed on top of a light bed or the like.

FIG. 6 is a schematic side elevation view of the pad like device with a portion of the pad like device broken away to show a smaller pad placed inside the pad like device containing a different fill material than the pad like device.

FIG. 7 is a fragmentary top plan view of the pad like device of FIG. 6 as seen from the plane of the line 7—7 thereof.

FIG. 8 is a fragmentary perspective view of the pad like device having one or more unfilled areas or holes that may be covered by a transparent or translucent window to allow more of the light from a light emitter to pass through these areas.

FIG. 9 is a schematic transverse section through the pad like device of FIG. 8.

DETAILED DESCRIPTION OF THE INVENTION

Figure 1:
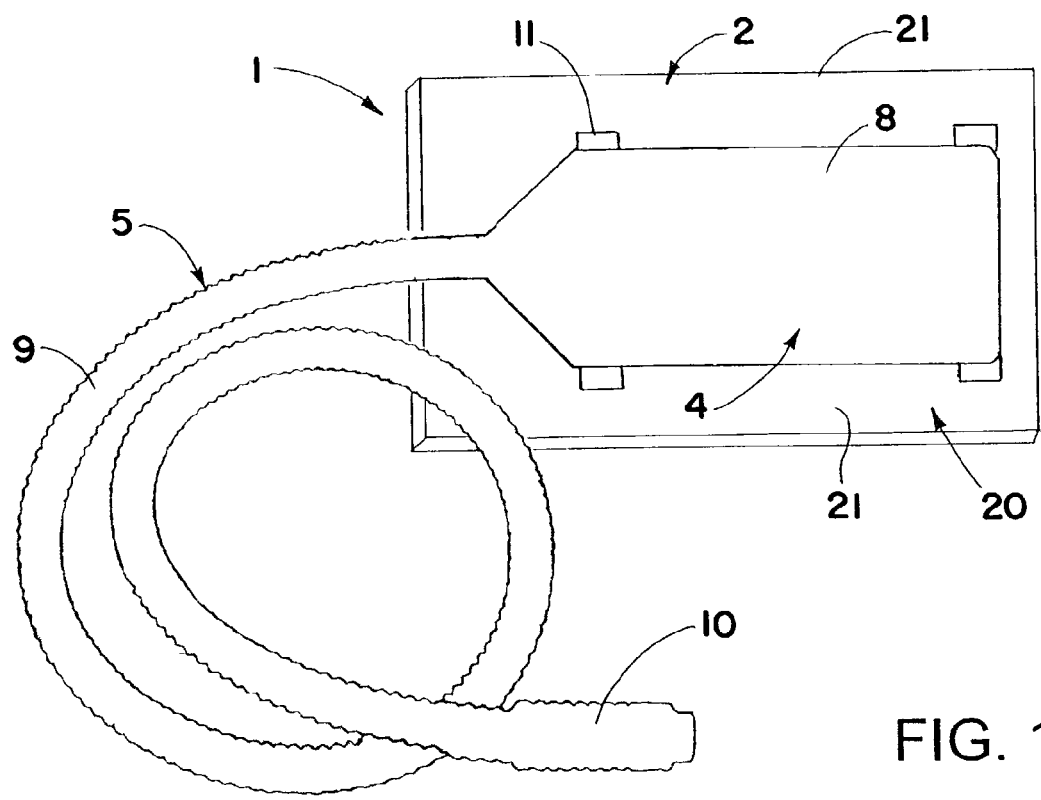
FIG. 1 is a schematic plan view of the pad like device of the present invention showing one type of light emitter attached to one side thereof.
Figure 4:
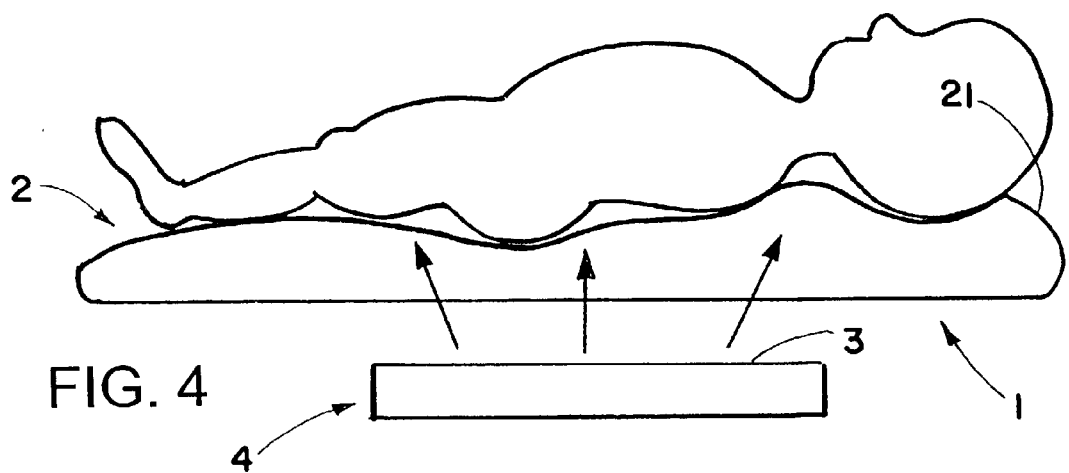
FIG. 4 is a schematic side elevation view showing the pad like device varying in thickness over its length and width.

Referring now in detail to the drawings, and initially to FIGS. 1 and 4, there is shown one form of device 1 in accordance with this invention for use during phototherapy treatment including a pad 2 that is placed over a light emitting surface 3 (see FIG. 4) of a light emitter 4 that receives light through a light distributor 5 from a suitable light source (not shown). Light emitter 4 and light distributor 5 may be formed of a flexible optic light guide which may either be a solid transparent optical member or comprised of a plurality of optical fibers as desired. Light emitting surface 3 of light emitter 4 is larger than the cross sectional area of light distributor 5 to reduce energy density by spreading the light over a larger surface area at the light emitting surface.

Figure 2:
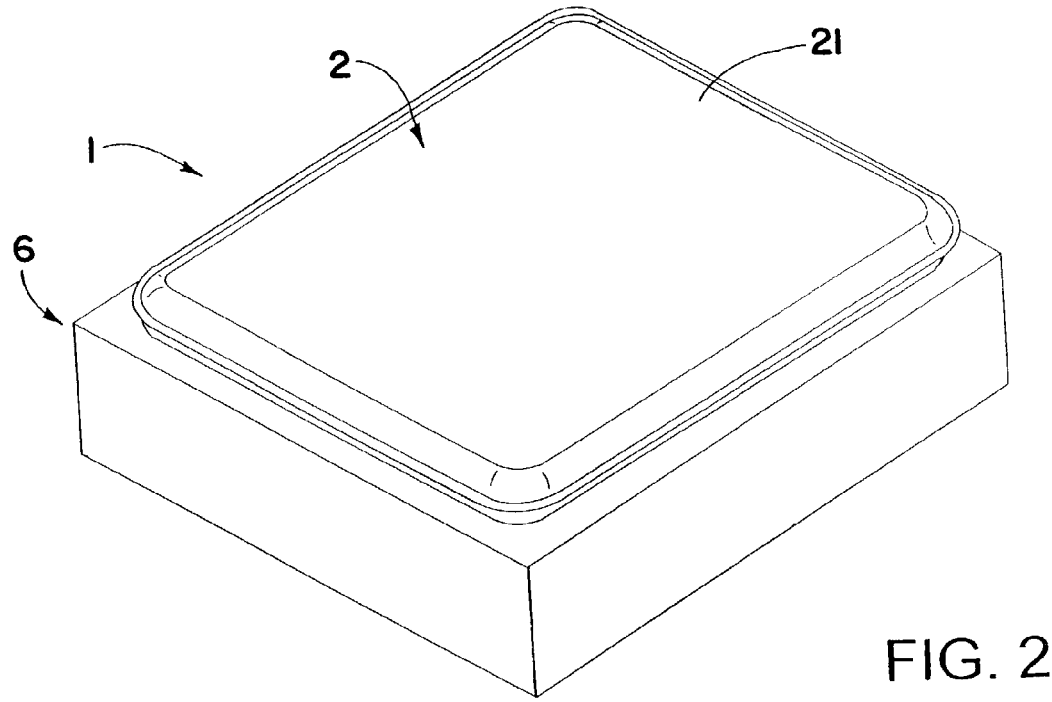

Light emitter 4 schematically shown in FIG. 1 is in the general shape of a relatively thin light panel having a greater width than thickness and opposite ends and sides and top and bottom surfaces, giving the light emitter increased flexibility. However, light emitter 4 may also comprise a light bed 6 as schematically shown in FIG. 2 and may be lit using light emitting diodes, a halogen light, fluorescents or other suitable light source.

A protective cover 8 made of a suitable flexible translucent or transparent material may surround the light emitter 4. Also, a protective sleeve 9 made of a flexible opaque or reflective material may surround the light distributor 5 for easy maneuverability to facilitate connection of a connector 10 or other suitable attachment device at the outer end of the light distributor to a remote light source for transmission of the light through the light distributor to the light emitter in a manner well known in the art. Suitable filters (not shown) may also be interposed between the light distributor and light source to filter out any undesired frequencies of light, for example, infrared or ultraviolet, allowing only those light frequencies desired to pass through the light distributor.

Figure 3:
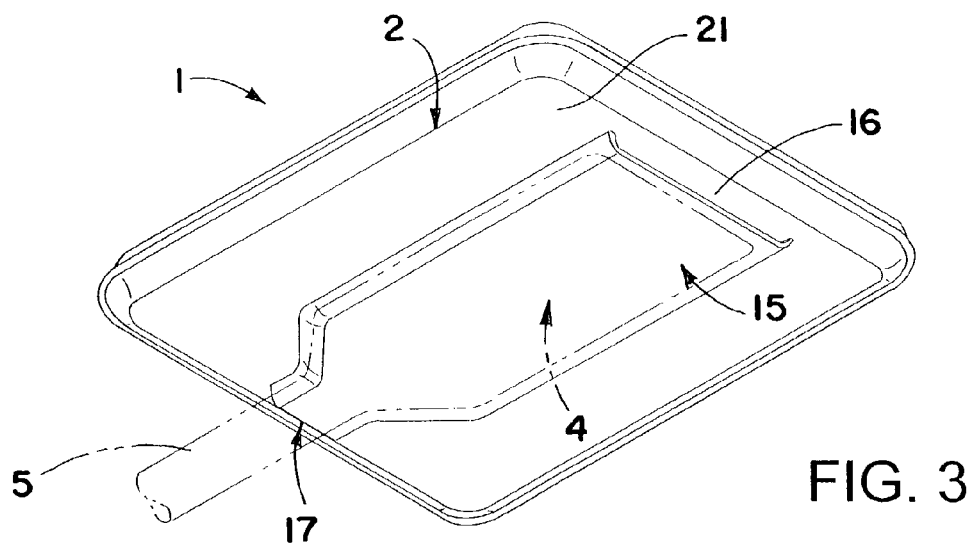
FIG. 3 is a schematic perspective view showing the pad like device with a pocket on one side for receipt of a light emitter.

Light emitter 4 may be removably attached to one side of the pad 2 using a suitable attachment device 11 such as an adhesive, a Velcro closure, a snap closure, or other mechanical fastener. Alternatively, where the light emitter 4 is relatively thin and lightweight, a pocket 15 may be provided on one side of the pad 2 having an opening 16 at one end of a width greater than the width of the light emitter and another opening 17 at the opposite end of a width less than the width of the light emitter 4 but greater than the width of the light distributor 5 for insertion of the light emitter into the pocket through the larger opening and threading of the light distributor out through the smaller opening as schematically shown in FIG. 3.

The pad 2 is filled with a suitable medium 20 (see FIG. 5) that provides the patient, usually an infant, with a softer surface to lie on than the light emitter for comfort and proper support for the patient during phototherapy. Examples of mediums that may be used as the fill material for the pad are air, water, liquid soap, gel, and silicone. A clear gel is preferred, in that it allows more of the light to pass from the light emitter 4 through the medium and also generally provides better support than most other mediums. The fill medium 20 is contained within a covering 21 made of a suitable flexible material such as urethane or polyvinyl chloride. Both the medium 20 and the pad covering 21 must be optically transparent or translucent, at least in those areas of the pad that are adapted to support those parts of the body of the patient that are to be treated with phototherapy.

Figure 5:
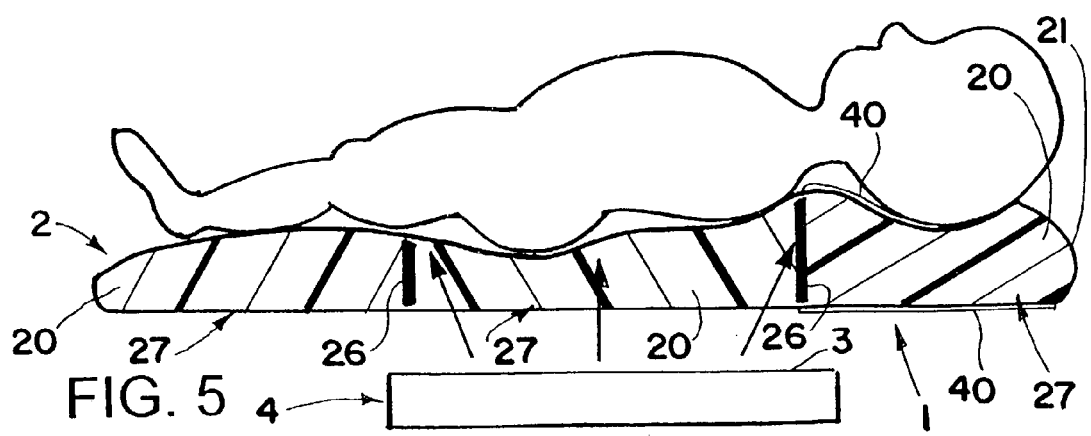
FIG. 5 is a schematic longitudinal section through the pad like device showing different chambers or compartments within the pad containing fill materials of different firmness or densities.

The pad 2 may be of varying thickness over its length and width as schematically shown in FIGS. 4–6 for proper patient support. Also, suitable baffles 26 or the like may extend between opposite sides inside the pad to form separate axially spaced chambers or compartments 27 extending between such opposite sides within the pad for receiving fill materials of different firmness or densities at different regions along the length of the pad as schematically shown in FIG. 5 for proper patient support. For example, the area of the pad that is adapted to support the hips of the patient may contain a fill material that is less firm or dense than the fill material in the area that is adapted to support the head of the patient, whereas the area of the pad that is adapted to support the legs of the patient may contain a fill material that is still less firm or dense, and so on.

An example of different fill materials that may be used in different areas of the pad are air in the area of the pad that is to be used as a head rest and a clear gel in other areas of the pad to better distribute the patient's weight over the remaining surface of the pad.

Also, air or other fill material 20' for supporting the head or other body part of the patient may be contained in a smaller pad 28 that is placed inside the larger pad 2 and surrounded by other fill material 20 as schematically shown in FIG. 6. The outer protective cover 29 of the smaller pad 28 may be made of the same material as the outer protective cover 21 of the larger pad 2 or of a different material as desired. The smaller pad 28 may be secured in place inside the larger pad 2 as by heat sealing the outer protective cover 29 of the smaller pad inside the larger pad along the side edges 31, 32 and 33, 34 of both pads as schematically shown in FIG. 7.

The fill material 20' in some areas of the pad 2 that support parts of the patient's body such as the head where no phototherapy is desired may be made opaque to block out the light from the phototherapy light emitter 4 as schematically shown in FIG. 6. Alternatively, those areas of the pad may be coated with an opaque or reflective material 40 to block out the light in those areas as schematically shown in FIG. 5.

Pad 2 may also have one or more unfilled areas or holes 41 which may but need not be covered by a transparent or translucent window 42 to allow a greater portion of the light from the phototherapy light emitter 4 to pass through these areas of the pad as schematically shown in FIGS. 8 and 9 to permit increased phototherapy of the body portions adapted to be supported by these areas as desired.

Figure 10:
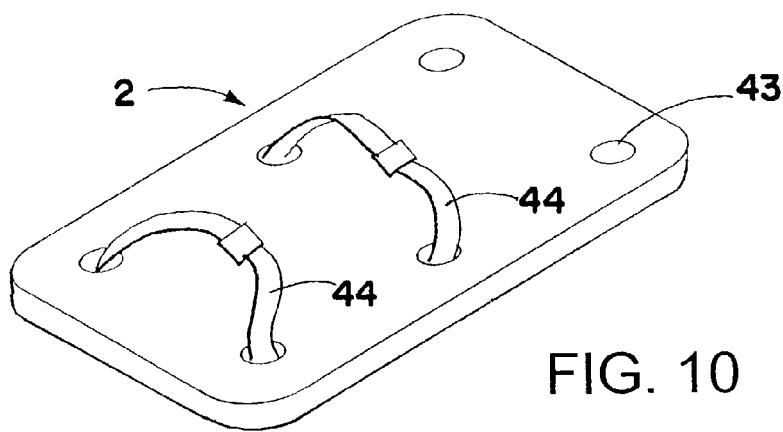
FIG. 10 is a fragmentary perspective view of the pad like device showing relatively small holes through the pad and straps for attaching the pad to a patient.

Also other smaller holes 43 may be provided in the pad as schematically shown in FIG. 10 to facilitate attachment of the pad to another surface or through which to route cable, tubing or other hardware or the like. Moreover, straps 44 may be attached to the pad 2 as further schematically shown in FIG. 10 to facilitate attachment of the pad to a patient.

Figure 11:
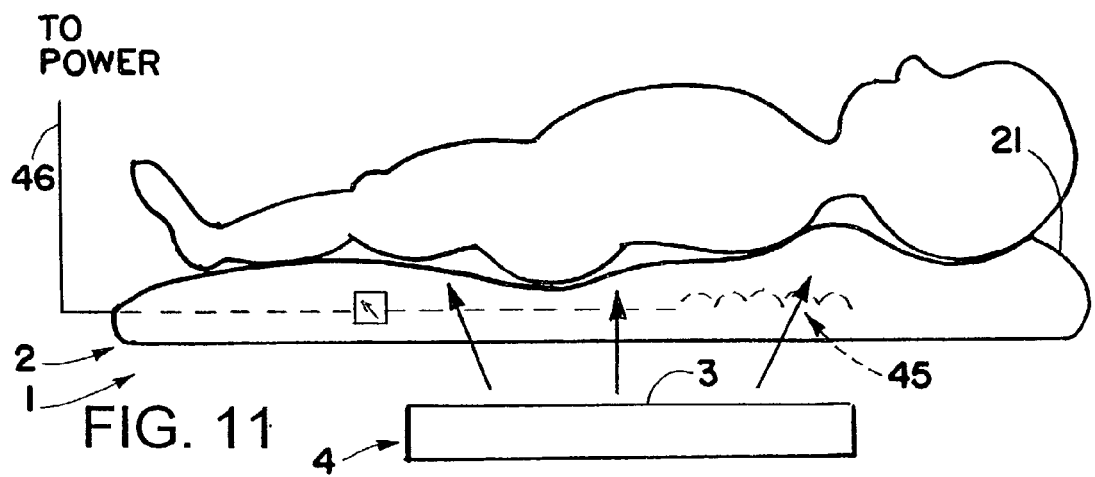
FIGS. 11 and 12 are schematic side elevation views of the pad like device containing a heating element and a heating and cooling element for heating or cooling the pad.
Figure 12:
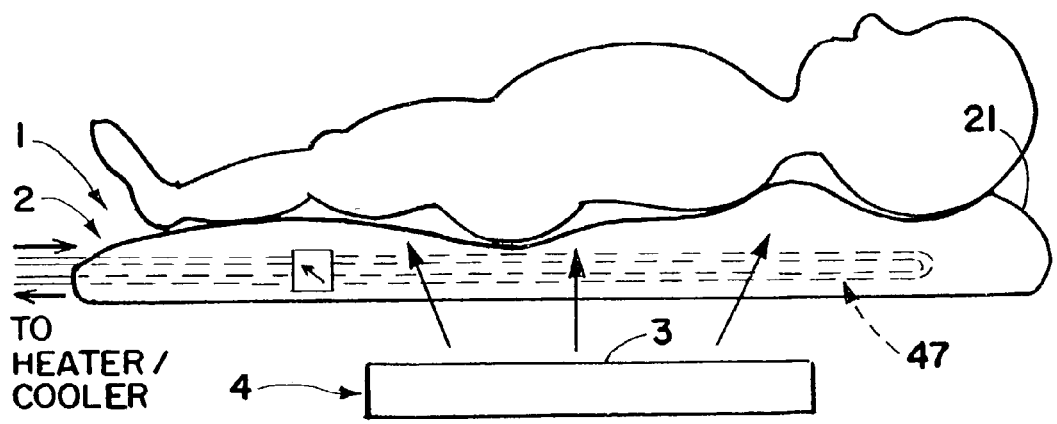

If desired, the pad 2 may contain a heating element and/or a cooling element for heating or cooling the pad as needed for patient comfort. FIG. 11 shows a thermostatically controlled electrical heating element 45 within the pad having a power cord 46 connected thereto for connection to a suitable power source for heating the pad, whereas FIG. 12 shows a thermostatically controlled heating or cooling loop 47 inside the pad through which a suitable heating or cooling fluid from a heater or cooler may be circulated for heating or cooling the pad as needed for patient comfort.

The dimensions of the pad will vary depending on the particular application. However, in one form of the invention, the pad may have a thickness of between approximately one-eighth inch and one-half inch, a width of approximately eight inches, and a length of approximately eleven inches.

Although the invention has been shown and described with respect to certain embodiments, it is obvious that equivalent alterations and modifications will occur to others skilled in the art upon the reading and understanding of the specification. In particular, with regard to the various functions performed by the above described components, the terms (including any reference to a "means") used to describe such components are intended to correspond, unless otherwise indicated, to any component which performs the specified function of the described component (e.g., that is functionally equivalent), even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness and different thickness for proper patient support.

2. The device of claim 1 wherein said pad has a flexible transparent or translucent protective cover containing said medium.

3. The device of claim 2 wherein said cover is made of at least one of urethane and polyvinyl chloride.

4. The device of claim 1 further comprising attachment means for attaching said pad to said light emitter.

5. The device of claim 4 wherein said attachment means comprises at least one of a hook and loop fastener, a snap closure, an adhesive and a mechanical fastener.

6. The device of claim 1 wherein said pad has straps for attaching said pad to a patient.

7. The device of claim 1 wherein said pad has at least one opaque area for blocking the passage of light emitted by said light emitter through said opaque area.

8. The device of claim 1 wherein said pad has at least one area covered with a reflective coating to block the passage of light emitted by said light emitter through said one area.

9. The device of claim 1 wherein said pad includes means for cooling said pad as needed for patient comfort.

10. The device of claim 1 wherein said medium is a clear gel.

11. The device of claim 1 wherein said medium is air.

12. The device of claim 1 wherein said medium is water.

13. The device of claim 1 wherein said medium is a clear silicone.

14. The device of claim 1 wherein said medium is a liquid soap.

15. The device of claim 1 wherein said pad has a pocket on one side for receipt of said light emitter.

16. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having different areas within said pad containing mediums of different firmness for proper patient support, and a smaller pad contained within said pad containing another medium to aid in providing proper patient support.

17. The device of claim 16 wherein said smaller pad is affixed within said pad.

18. The device of claim 17 wherein said smaller pad is heat sealed inside said pad.

19. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having different areas within said pad containing mediums of different firmness at different regions along the length of said pad for proper patient support, said different areas within said pad being formed by separate axially spaced chambers within said pad extending between opposite sides of said pad.

20. The device of claim 19 wherein at least some of said chambers contain different mediums.

21. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having different areas within said pad containing mediums of different firmness at different regions along the length of said pad for proper patient support, said different areas within said pad being formed by axially spaced baffles within said pad extending between opposite sides of said pad.

22. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, said pad having at least one area that is devoid of any medium to allow a greater amount of the light emitted by said light emitter to pass through said pad at said one area.

23. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, said pad having a hole at least at one area to allow a greater amount of the light emitted from said light emitter to pass through said hole at said one area.

24. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, and a transparent or translucent window in said pad at least at one area to allow a greater amount of the light emitted by said light emitter to pass through said window at said one area.

25. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, and attachment means for attaching said pad to said light emitter, said attachment means comprising a pocket in one side of said pad for receipt of said light emitter.

26. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, said pad having holes to facilitate attachment of said pad to another surface.

27. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, said pad having holes through which to route at least one of: cable, tubing and hardware.

28. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having areas of different firmness at different regions along the length of said pad for proper support of different parts of a patient's body, said pad including means for heating said pad as needed for patient comfort.

29. A device for use during phototherapy treatment of a patient comprising a pad adapted to be placed over a phototherapy light emitter, said pad containing a medium that provides a comfortable support for the patient during phototherapy treatment, said pad having at least one area that is transparent or translucent to allow a portion of the light emitted by said light emitter to pass through said pad for phototherapy treatment, said pad having different areas within said pad containing mediums of different firmness at different regions along the length of said pad for proper patient support, said pad having a pocket on one side for receipt of a phototherapy light emitter, said pocket having different size openings at opposite ends, the opening at one end being larger than the opening at the other end.

* * * * *